(12) United States Patent
Darimont et al.

(10) Patent No.: US 8,440,178 B2
(45) Date of Patent: *May 14, 2013

(54) LACTOBACILLUS RHAMNOSUS AND WEIGHT CONTROL

(75) Inventors: Christian Darimont, Lausanne (CH); David Philippe, Lausanne (CH); Catherine Mace, Lausanne (CH); Fabrizio Arigoni, Tokyo (JP)

(73) Assignee: Nestec S.A., Vevey (CH)

( * ) Notice: Subject to any disclaimer, the term of this patent is extended or adjusted under 35 U.S.C. 154(b) by 350 days.

This patent is subject to a terminal disclaimer.

(21) Appl. No.: 12/672,952

(22) PCT Filed: Jul. 24, 2008

(86) PCT No.: PCT/EP2008/059755
§ 371 (c)(1), (2), (4) Date: May 26, 2010

(87) PCT Pub. No.: WO2009/021824
PCT Pub. Date: Feb. 19, 2009

(65) Prior Publication Data
US 2012/0114622 A1    May 10, 2012

(30) Foreign Application Priority Data
Aug. 10, 2007  (EP) .................... 07114153

(51) Int. Cl.
A01N 63/00   (2006.01)
A01N 63/02   (2006.01)
A61K 35/00   (2006.01)
A23C 9/12    (2006.01)
C12N 1/20    (2006.01)

(52) U.S. Cl.
USPC ......... 424/93.3; 424/93.45; 424/780; 426/61; 435/252.9

(58) Field of Classification Search .............. None
See application file for complete search history.

(56) References Cited

U.S. PATENT DOCUMENTS

| 7,001,756 | B1 | 2/2006 | Hsu et al. | |
| 2004/0001898 | A1* | 1/2004 | Malnoe et al. | 424/764 |
| 2004/0062758 | A1* | 4/2004 | Mayra-Makinen et al. | 424/93.45 |
| 2004/0161422 | A1* | 8/2004 | Ranganathan | 424/93.45 |
| 2005/0100617 | A1* | 5/2005 | Malnoe et al. | 424/728 |

FOREIGN PATENT DOCUMENTS

| CN | 1670183 | 9/2005 |
| WO | WO2006019222 | 2/2006 |
| WO | WO2006108824 | 10/2006 |
| WO | WO2007135141 | 11/2007 |
| WO | WO2008116700 | 10/2008 |

OTHER PUBLICATIONS

International Search Report PCT/EP2008/059755 dated Dec. 19, 2008, 4 pages.
European Search Report Appl. No. / Patent No. 07114153.5-1521 dated Jan. 25, 2008, 3 pages.
Written Opinion of the International Searching Authority PCT/EP2008/059755 dated Dec. 19, 2008, 6 pages.
Fuller et al., "Modification of the Intestinal Microflora Using Probiotics and Prebiotics," Scand J Gastroenterol, vol. 32; Suppl. vol. 222, pp. 28-31, (1997).
Turnbaugh et al., "Human gut microbes associated with obesity," Nature, vol. 444, Issue 21/28, Dec. 2006, pp. 1022-1023.
Turnbaugh et al., "An obesity-associate gut microbiome with increased capacity for energy harvest," Nature, vol. 444, Issue 21/28, Dec. 2006, pp. 1027-1031.
Salminen et al., "Probiotics: how should they be defined?," Trends in Food Science & Technology, vol. 10 (1999), pp. 107-110.

* cited by examiner

*Primary Examiner* — Chris R Tate
*Assistant Examiner* — Douglas F White
(74) *Attorney, Agent, or Firm* — K&L Gates LLP

(57) ABSTRACT

The present invention generally relates to the field of obesity. In particular the present invention relates to the use of probiotics to treat obesity. One embedment of the present invention relates to the use of *Lactobacillus rhamnosus* CGMCC 1.3724 and/or *Lactobacillus rhamnosus* NCC 4007 for the preparation of a composition to support weight management, promote weight loss and/or to treat obesity.

15 Claims, 5 Drawing Sheets

LACTOBACILLUS RHAMNOSUS AND WEIGHT CONTROL

The present invention generally relates to the field of obesity. In particular the present invention relates to the use of probiotics to support weight management, promote weight loss and/or to treat obesity.

During the past decades, the prevalence of obesity has increased worldwide to epidemic proportion. Approximately 1 billion of people worldwide are overweight or obese, conditions that increase mortality, mobility and economical costs. Obesity develops when energy intake is greater than energy expenditure, the excess energy being stored mainly as fat in adipose tissue. Body weight loss and prevention of weight gain can be achieved by reducing energy intake or bioavailability, increasing energy expenditure and/or reducing storage as fat. Obesity represents a serious threat to health because it is associated with an array of chronic diseases, including diabetes, atherosclerosis, degenerative disorders, airway diseases and some cancers.

Modifications of the intestinal flora were recently associated with obesity. These changes were demonstrated in obese mice to affect the metabolic potential of gut microbiota resulting in an increased capacity to harvest energy from the diet (Turnbaugh P J, Ley R E, Mahowald M A, Magrini V, Mardis E R, Gordon J I. An obesity-associated gut microbiome with increased capacity for energy harvest. Nature. 2006; Ley R E, Turnbaugh P J, Klein S, Gordon J I. Microbial ecology: human gut microbes associated with obesity. Nature. 2006). Such modifications of gut microbiota are proposed to contribute to the pathophysiology of obesity. Probiotics, the beneficial bacteria present in food or food supplements, are known to modify the intestinal microbiota (Fuller R & Gibson G R. Modification of the intestinal microflora using probiotics and prebiotics. Scand J. Gastroenterol. 1997).

WO2006019222 discloses the *Lactobacillus* rhamnosus Strain PL60 KCCM-10654P with a body-fat reducing activity that overproduces t10c12-octadecadienoic acid.

However the overproduction of t10c12-octadecadienoic acid might be problematic for patients that react sensitively on t10c12-octadecadienoic acid.

U.S. Pat. No. 7,001,756 and CN1670183 provide an isolated microorganism strain, *Lactobacillus rhamnosus* GM-020, which is found to be effective in treating obesity.

Based on this prior art it was the object of the present invention to identify alternative probiotic bacteria that do not rely on the overexpression of t10c12-octadecadienoic acid and/or that offer an attractive effectiveness that can be used to treat obesity and that overcomes disadvantages of the strains of the prior art.

This object is achieved by the use of claim 1.

The present inventors have found that—unexpectedly—the strain *Lactobacillus rhamnosus* CGMCC 1.3724 or the strain *Lactobacillus rhamnosus* NCC 4007 achieves this object.

Hence, one embodiment of the present invention is the use of *Lactobacillus rhamnosus* CGMCC 1.3724 or *Lactobacillus rhamnosus* NCC 4007 for the preparation of a composition to treat obesity in animals.

A further embodiment of the present invention is the use of *Lactobacillus rhamnosus* CGMCC 1.3724 or *Lactobacillus rhamnosus* NCC 4007 for the preparation of a composition to promote weight loss.

Still, a further embodiment of the present invention is the use of *Lactobacillus rhamnosus* CGMCC 1.3724 or *Lactobacillus rhamnosus* NCC 4007 for the preparation of a composition to support weight management.

The compositions described in the framework of the present invention are in particular beneficial for long term application. The inventors have for example shown in an animal model that a mouse treated with the composition described in the present invention will put on significantly less weight than a control mouse. This effect was even more pronounced the longer the composition was administered. The experiment was continued for about two months and the observed effects increased with time.

Consequently, in a preferred embodiment of the present invention, the composition is to be administered for at least 2 weeks, at least 3 weeks, at least 4 weeks, at least 5 weeks, at least 6 weeks, at least 7 weeks, and/or at least 8 weeks.

In this specification, the following terms have the following meanings:

"Animal" means animals including humans.

The term "*Lactobacillus rhamnosus* CGMCC 1.3724" is meant to include the bacterium, a cell growth medium with the bacterium or a cell growth medium in which *Lactobacillus rhamnosus* CGMCC 1.3724 was cultivated.

The term "*Lactobacillus rhamnosus* NCC 4007" is meant to include the bacterium, a cell growth medium with the bacterium or a cell growth medium in which *Lactobacillus rhamnosus* NCC 4007 was cultivated.

"Body mass index" or "BMI" means the ratio of weight in Kg divided by the height in metres, squared.

"Overweight" is defined for an adult human as having a BMI between 25 and 30.

"Obesity" is a condition in which the natural energy reserve, stored in the fatty tissue of animals, in particular humans and other mammals, is increased to a point where it is associated with certain health conditions or increased mortality. "Obese" is defined for an adult human as having a BMI greater than 30.

"Probiotic" means microbial cell preparations or components of microbial cells with a beneficial effect on the health or well-being of the host. (Salminen S, Ouwehand A. Benno Y. et al "Probiotics: how should they be defined" Trends Food Sci. Technol. 1999:10 107-10).

"Prebiotic" means food substances intended to promote the growth of probiotic bacteria in the intestines.

"Food grade bacteria" means bacteria that are used and generally regarded as safe for use in food.

"Weight loss" in the context of the present invention is a reduction of the total body weight. Weight loss may for example refer to the loss of total body mass in an effort to improve fitness, health, and/or appearance.

"Weight management" or "weight maintenance" relates to maintaining a total body weight. For example, weight management may relate to maintaining a BMI in the area of 18.5-25 which is considered to be normal.

The composition of the present invention may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents, gel forming agents, antioxidants and antimicrobials. The composition may also contain conventional pharmaceutical additives and adjuvants, excipients and diluents, including, but not limited to, water, gelatine of any origin, vegetable gums, ligninsulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like. In all cases, such further components will be selected having regard to their suitability for the intended recipient.

The composition may be a nutritionally complete formula.

The composition according to the invention may comprise a source of protein.

Any suitable dietary protein may be used, for example animal proteins (such as milk proteins, meat proteins and egg proteins); vegetable proteins (such as soy protein, wheat protein, rice protein, and pea protein); mixtures of free amino acids; or combinations thereof. Milk proteins such as casein and whey, and soy proteins are particularly preferred.

The proteins may be intact or hydrolysed or a mixture of intact and hydrolysed proteins. It may be desirable to supply partially hydrolysed proteins (degree of hydrolysis between 2 and 20%), for example for animals believed to be at risk of developing cows' milk allergy. If hydrolysed proteins are required, the hydrolysis process may be carried out as desired and as is known in the art. For example, a whey protein hydrolysate may be prepared by enzymatically hydrolysing the whey fraction in one or more steps. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source.

The composition may also contain a source of carbohydrates and a source of fat.

If the composition includes a fat source, the fat source preferably provides 5% to 40% of the energy of the composition; for example 20% to 30% of the energy. A suitable fat profile may be obtained using a blend of canola oil, corn oil and high-oleic acid sunflower oil.

A source of carbohydrate may be added to the composition.

The source of carbohydrates preferably provides 40% to 80% of the energy of the composition. Any suitable carbohydrate may be used, for example sucrose, lactose, glucose, fructose, corn syrup solids, maltodextrins, and mixtures thereof. Dietary fibre may also be added if desired. Dietary fibre passes through the small intestine undigested by enzymes and functions as a natural bulking agent and laxative. Dietary fibre may be soluble or insoluble and in general a blend of the two types is preferred. Suitable sources of dietary fibre include soy, pea, oat, pectin, guar gum, gum Arabic, fructooligosaccharides, galacto-oligosaccharides, sialyl-lactose and oligosaccharides derived from animal milks. A preferred fibre blend is a mixture of inulin with shorter chain fructo-oligosaccharides. Preferably, if fibre is present, the fibre content is between 2 and 40 g/l of the composition as consumed, more preferably between 4 and 10 g/l.

The composition may also contain minerals and micronutrients such as trace elements and vitamins in accordance with the recommendations of Government bodies such as the USRDA. For example, the composition may contain per daily dose one or more of the following micronutrients in the ranges given:—300 to 500 mg calcium, 50 to 100 mg magnesium, 150 to 250 mg phosphorus, 5 to 20 mg iron, 1 to 7 mg zinc, 0.1 to 0.3 mg copper, 50 to 200 µg iodine, 5 to 15 µg selenium, 1000 to 3000 µg beta carotene, 10 to 80 mg Vitamin C, 1 to 2 mg Vitamin B1, 0.5 to 1.5 mg Vitamin B6, 0.5 to 2 mg Vitamin B2, 5 to 18 mg niacin, 0.5 to 2.0 µg Vitamin B12, 100 to 800 µg folic acid, 30 to 70 µg biotin, 1 to 5 µg Vitamin D, 3 to 10 µg Vitamin E.

One or more food grade emulsifiers may be incorporated into the composition if desired; for example diacetyl tartaric acid esters of mono- and di-glycerides, lecithin and mono- and di-glycerides. Similarly suitable salts and stabilisers may be included.

The composition is preferably orally or enterally administrable; for example in the form of a powder for re-constitution with milk or water.

Preferably, the composition is provided in the form of a powder, e.g., a shelf stable powder. Shelf stability can be obtained, for example by providing the composition with a water activity smaller than 0.2, for example in the range of 0.19-0.05, preferably smaller than 0.15.

Water activity or $a_w$ is a measurement of the energy status of the water in a system. It is defined as the vapor pressure of water divided by that of pure water at the same temperature; therefore, pure distilled water has a water activity of exactly one.

The composition described above may be prepared in any suitable manner. For example, it may be prepared by blending together the protein, the carbohydrate source, and the fat source in appropriate proportions. If used, the emulsifiers may be included at this point. The vitamins and minerals may be added at this point but are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The temperature of the water is conveniently about 50° C. to about 80° C. to aid dispersal of the ingredients. Commercially available liquefiers may be used to form the liquid mixture. The liquid mixture is then homogenised; for example in two stages.

The liquid mixture may then be thermally treated to reduce bacterial loads, by rapidly heating the liquid mixture to a temperature in the range of about 80° C. to about 150° C. for about 5 seconds to about 5 minutes, for example. This may be carried out by steam injection, autoclave or by heat exchanger; for example a plate heat exchanger.

Then, the liquid mixture may be cooled to about 60° C. to about 85° C.; for example by flash cooling. The liquid mixture may then be again homogenised; for example in two stages at about 10 MPa to about 30 MPa in the first stage and about 2 MPa to about 10 MPa in the second stage. The homogenised mixture may then be further cooled to add any heat sensitive components; such as vitamins and minerals. The pH and solids content of the homogenised mixture are conveniently adjusted at this point.

The homogenised mixture is transferred to a suitable drying apparatus such as a spray drier or freeze drier and converted to powder. The powder should have a moisture content of less than about 5% by weight.

*Lactobacillus rhamnosus* CGMCC 1.3724 or *Lactobacillus rhamnosus* NCC 4007 may be cultured according to any suitable method and prepared for addition to the composition by freeze-drying or spray-drying for example. Appropriate culturing methods for *Lactobacillus rhamnosus* CGMCC 1.3724 or *Lactobacillus rhamnosus* NCC 4007 are known to those skilled in the art. Alternatively, bacterial preparations can be bought from specialist suppliers such as Christian Hansen and Danisco already prepared in a suitable form for addition to food products such as nutritional and infant formulas. The probiotic bacteria may be added to the formula in an appropriate amount, preferably between $10^2$ and $10^{12}$ cfu/g powder, more preferably between $10^7$ and $10^{12}$ cfu/g powder.

In one embodiment of the present invention the animals to be treated with the composition prepared by the use of the present invention are at least two years old. This age limit applies in particular to humans. If the animals to be treated with the composition prepared by the use of the present invention are dogs or cats, for example, the dog or cat should be at least 4 months old.

In one embodiment of the present invention the composition is a medicament. As a medicament the dosage of *Lactobacillus rhamnosus* CGMCC 1.3724 and/or *Lactobacillus rhamnosus* NCC 4007 can be carefully adjusted according to a doctor's recommendation.

The composition prepared according to the present may also be a food product. As a food product the beneficial effects of *Lactobacillus rhamnosus* CGMCC 1.3724 or *Lactobacillus rhamnosus* NCC 4007 would be available to everyone. Treatment of obesity could be initiated at a much earlier stage. Further in a food product *Lactobacillus rhamnosus* CGMCC 1.3724 or *Lactobacillus rhamnosus* NCC 4007 would be even more pleasant to consume. Examples of food products that are applicable to the present invention are yoghurts, milk, flavoured milk, ice cream, ready to east desserts, powders for re-constitution with, e.g., milk or water, chocolate milk drinks, malt drinks, ready-to-eat dishes, instant dishes or drinks for humans or food compositions representing a complete or a partial diet intended for pets or livestock.

Consequently, in one embodiment the composition according to the present invention is a food product intended for humans, pets or livestock. In particular the composition is intended for animals selected from the group consisting of dogs, cats, pigs, cattle, horses, goats, sheep, poultry or humans, and in a preferred embodiment is the composition a food product intended for adult species, in particular human adults.

The composition of the present invention may also comprise at least one other kind of other food grade bacteria or yeast. The food grade bacteria may be probiotic bacteria and are preferably selected from the group consisting of lactic acid bacteria, bifidobacteria, propionibacteria or mixtures thereof. Probiotic bacteria may be any lactic acid bacteria or Bifidobacteria with established probiotic characteristics. For example they may be also capable of promoting the development of a bifidogenic intestinal microbiota. Suitable probiotic Bifidobacteria strains include *Bifidobacterium lactis* CNCM I-3446 sold inter alia by the Christian Hansen company of Denmark under the trade mark Bb12, *Bifidobacterium longum* ATCC BAA-999 sold by Morinaga Milk Industry Co. Ltd. of Japan under the trade mark BB536, the strain of *Bifidobacterium breve* sold by Danisco under the trade mark Bb-03, the strain of *Bifidobacterium breve* sold by Morinaga under the trade mark M-16V and the strain of *Bifidobacterium breve* sold by Institut Rosell (Lallemand) under the trade mark R0070. A mixture of suitable probiotic lactic acid bacteria and Bifidobacteria may be used.

As food grade yeast the following can be used for example *Saccharomyces cerevisiae* and/or *Saccharomyces boulardii*.

In a preferred embodiment of the present invention the composition further contains at least one prebiotic. Prebiotics can promote the growth of certain food grade bacteria, in particular of probiotic bacteria, in the intestines and can hence enhance the effect of *Lactobacillus rhamnosus* CGMCC 1.3724 and/or *Lactobacillus rhamnosus* NCC 4007. Furthermore, several prebiotics have a positive influence on, e.g., digestion.

Preferably the prebiotic is selected from the group consisting of oligosaccharides and optionally contain fructose, galactose, mannose, soy and/or inulin; dietary fibers; or mixtures thereof.

One advantage of the present invention is that *Lactobacillus rhamnosus* CGMCC 1.3724 and/or *Lactobacillus rhamnosus* NCC 4007 are effective, both, as living bacterium as well as inactivated bacterial species. Consequently, even conditions that will not allow the presence of living bacteria will not abolish the effectiveness of *Lactobacillus rhamnosus* CGMCC 1.3724 or *Lactobacillus rhamnosus* NCC 4007.

It is preferred, however that at least a part of the *Lactobacillus rhamnosus* CGMCC 1.3724 and/or *Lactobacillus rhamnosus* NCC 4007 are alive in the composition and preferably arrive alive in the intestine. This way they can colonize the intestine and increase their effectiveness by multiplication.

However, for special sterile food products or medicaments it might be preferable that *Lactobacillus rhamnosus* CGMCC 1.3724 and/or *Lactobacillus rhamnosus* NCC 4007 are not alive in the composition. Hence, in one embodiment of the present invention at least a part of the *Lactobacillus rhamnosus* CGMCC 1.3724 and/or *Lactobacillus rhamnosus* NCC 4007 are not alive in the composition.

*Lactobacillus rhamnosus* CGMCC 1.3724 or *Lactobacillus rhamnosus* NCC 4007 will be effective in any concentration. If *Lactobacillus rhamnosus* CGMCC 1.3724 or *Lactobacillus rhamnosus* NCC 4007 reaches the intestine alive a single bacterium can be sufficient to achieve a powerful effect by colonization and multiplication.

However, for a medicament it is generally preferred that a daily dose of the medicament comprises between $10^2$ and $10^{12}$ cfu of *Lactobacillus rhamnosus* CGMCC 1.3724 or *Lactobacillus rhamnosus* NCC 4007. A particular suitable daily dose of *Lactobacillus rhamnosus* CGMCC 1.3724 or *Lactobacillus rhamnosus* NCC 4007 is from $10^5$ to $10^{11}$ colony forming units (cfu), more preferably from $10^7$ to $10^{10}$ cfu.

In the case of inactivated *Lactobacillus rhamnosus* CGMCC 1.3724 or *Lactobacillus rhamnosus* NCC 4007 it is generally preferred that a daily dose of the medicament comprises between $10^2$ and $10^{12}$ cells of *Lactobacillus rhamnosus* CGMCC 1.3724 or *Lactobacillus rhamnosus* NCC 4007. A particular suitable daily dose of *Lactobacillus rhamnosus* CGMCC 1.3724 or *Lactobacillus rhamnosus* NCC 4007 is from $10^5$ to $10^{11}$ cells, more preferably from $10^7$ to $10^{10}$ cells.

For a food composition it is generally preferred that it comprises between $10^3$ and $10^{12}$ cfu of *Lactobacillus rhamnosus* CGMCC 1.3724 or *Lactobacillus rhamnosus* NCC 4007 per g of the dry weight of the food composition. A particular suitable amount of *Lactobacillus rhamnosus* CGMCC 1.3724 or *Lactobacillus rhamnosus* NCC 4007 is from $10^5$ to $10^{11}$ cfu per g of the dry weight of the food composition, more preferably from $10^7$ to $10^{10}$ cfu per g of the dry weight of the food composition.

In the case of inactivated *Lactobacillus rhamnosus* CGMCC 1.3724 or *Lactobacillus rhamnosus* NCC 4007 it is generally preferred that the food composition comprises between $10^3$ and $10^{12}$ cells of *Lactobacillus rhamnosus* CGMCC 1.3724 or *Lactobacillus rhamnosus* NCC 4007 per g of the dry weight of the food composition. A particular suitable amount of *Lactobacillus rhamnosus* CGMCC 1.3724 or *Lactobacillus rhamnosus* NCC 4007 is from $10^5$ to $10^{11}$ cells per g of the dry weight of the food composition, more preferably from $10^7$ to $10^{10}$ cells per g of the dry weight of the food composition.

The daily dose of *Lactobacillus rhamnosus* CGMCC 1.3724 or *Lactobacillus rhamnosus* NCC 4007 in a composition will depend on the particular person or animal to be treated. Important factors to be considered include age, body weight, sex and health condition.

For example a typical daily dose of *Lactobacillus rhamnosus* CGMCC 1.3724 or *Lactobacillus rhamnosus* NCC 4007 in a composition will be in the range of $10^4$-$10^{12}$ cfu and/or cells per day, preferably $10^6$-$10^{10}$ cfu and/or cells per day, preferably $10^7$-$10^9$ cfu and/or cells per day.

A further use of a composition comprising *Lactobacillus rhamnosus* CGMCC 1.3724 or *Lactobacillus rhamnosus* NCC 4007 according to the present invention is to support weight loss and/or weight maintenance.

Since establishing and maintaining a proper body weight and—in particular—an acceptable weight percentage of fat in the body is a key step to treat or prevent metabolic disorders, a further use of a composition comprising *Lactobacillus rhamnosus* CGMCC 1.3724 or *Lactobacillus rhamnosus* NCC 4007 according to the present invention is to treat or prevent metabolic disorders.

In particular, a composition comprising *Lactobacillus rhamnosus* CGMCC 1.3724 or *Lactobacillus rhamnosus* NCC 4007 according to the present invention can be used to treat or prevent diabetes, hypertension and/or cardiovascular diseases and can hence make a significant contribution to the well-being of today's population in a number countries, in particular in well developed countries.

It is clear to those skilled in the art that any features described in this specification can be combined freely without departing from the scope of the present invention as disclosed.

Further features and advantages of the present invention result from the following Examples and Figures.

EXAMPLE 1

Six to eight weeks-old male obese Zucker rats (n=12) fed a chow diet were treated with $10^9$-$10^{10}$ cfu *Lactobacillus rhamnosus* CGMCC 1.3724 per day for 60 days. *Lactobacillus rhamnosus* NCC-4007 biomass diluted in the (deMan Rogosa Sharpe) MRS medium was administrated in the drinking solution containing NaCl 9/1000, the control group received the saline solution with corresponding amount of MRS medium present in the probiotic preparation. Body weight was followed during the study and body composition, assessed by NMR, was measured before and at the end of the treatment. The glucose tolerance was assessed at the end of the intervention by performing an Intra-peritoneal Glucose Tolerance Test (IPGTT), which consists of administrating a 20% D-glucose solution through an intra-peritoneal injection to 16 hours-fasted rats and to collect blood samples from the tail vein at 0, 15, 30, 60 and 120 min. after the injection. Glucose was then measured at the different time points.

Figure 1:
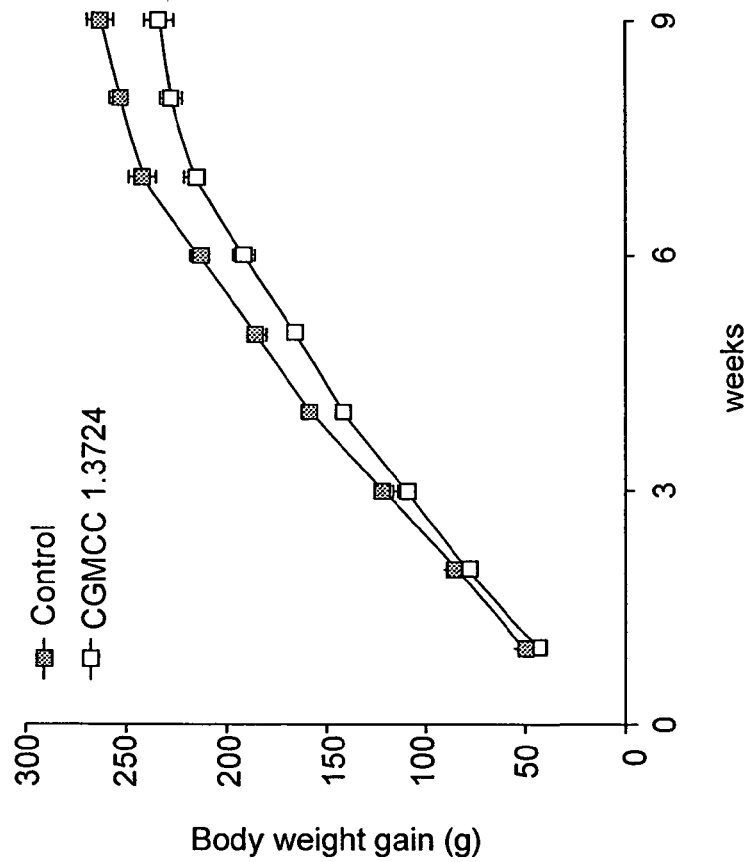
FIG. 1 shows that rats receiving the CGMCC 1.3724 strain had a significant reduction of weight gain (11%) as compared with the control group. Body weight gain is measured versus time.

FIG. 1 shows that rats receiving the CGMCC 1.3724 strain had a significant reduction of weight gain (11%) as compared with the control group.

Figure 2:
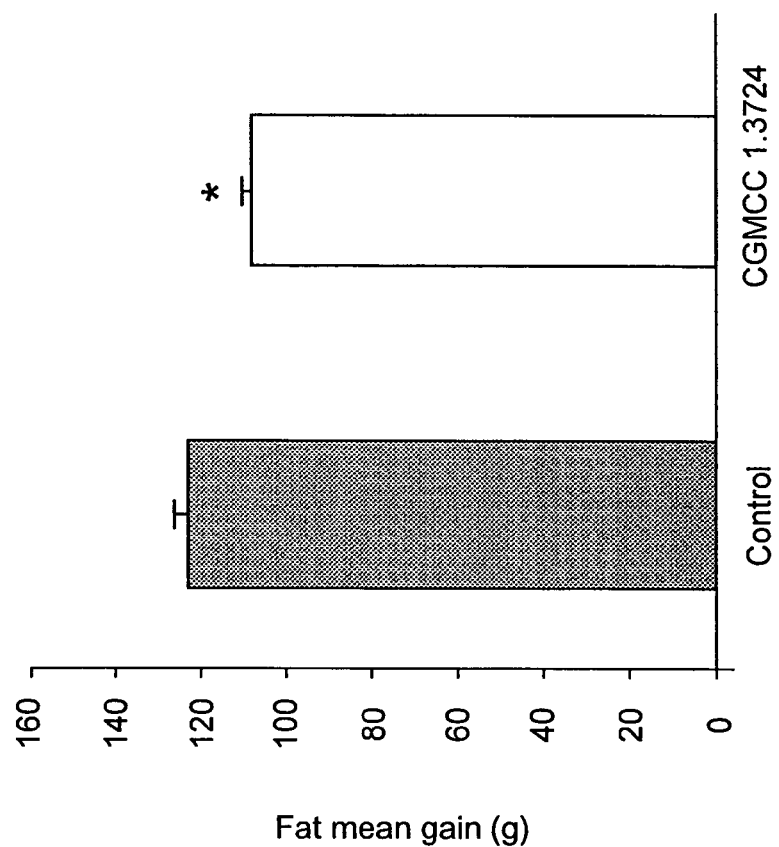
FIG. 2 shows the fat mass gain of the mice of FIG. 1.

The effect on weight gain was associated to a lower fat mass gain (FIG. 2).

Figure 3:
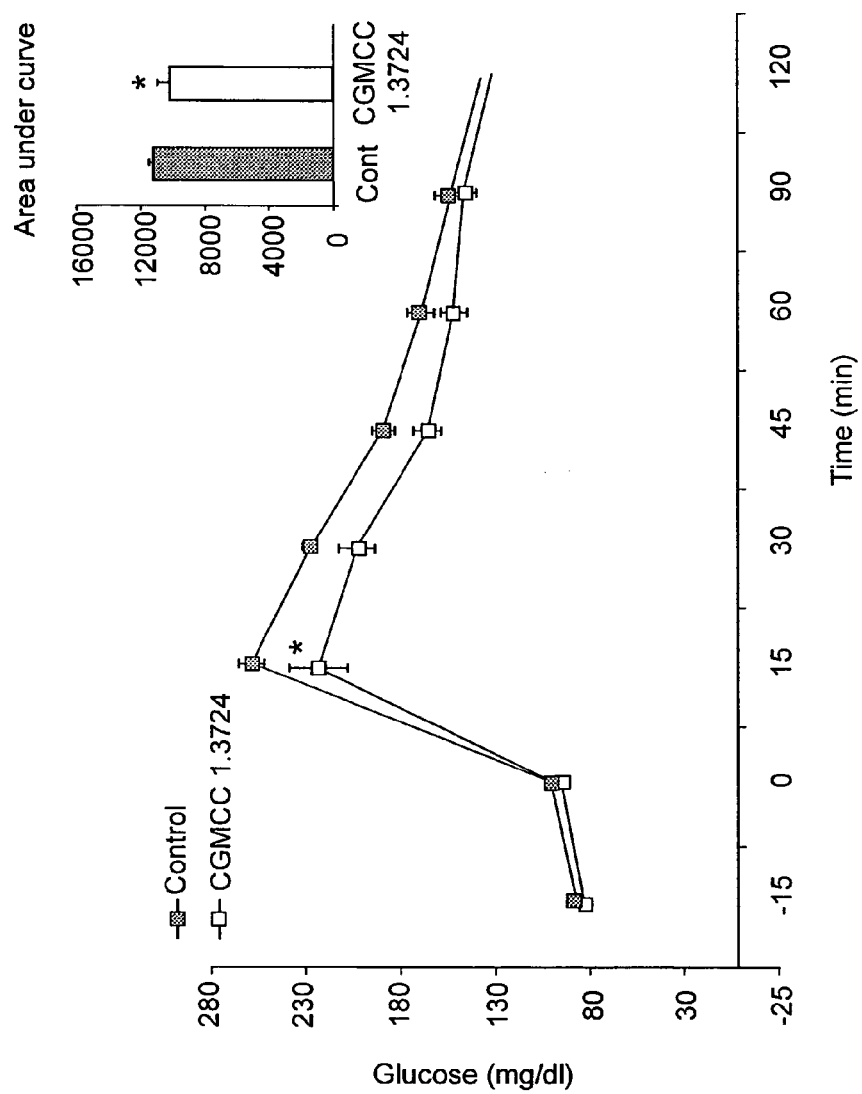
FIG. 3 shows the result of a glucose tolerance test with the mice of FIG. 1.

The glucose tolerance of these obese rats was improved by CGMCC 1.3724 strain administration, as represented by a smaller area under the curve (FIG. 3).

Identical Experiments with *Lactobacillus rhamnosus* NCC 4007 gave similar results.

EXAMPLE 2

Seven to eight weeks-old male obese ob/ob mice or their lean heterozygous littermate ob/+ mice were fed a chow diet and treated with $10^9$-$10^{10}$ cfu *Lactobacillus rhamnosus* NCC-4007 per day for 60 days. *Lactobacillus rhamnosus* CGMCC 1.3724 biomass diluted in the MRS medium was administrated in the drinking solution containing NaCl 9/1000, the control group received the saline solution with corresponding amount of MRS medium present in the probiotic preparation. Body weight was followed during the study and body composition, assessed by NMR, was measured before and at the end of the treatment.

Figure 4:
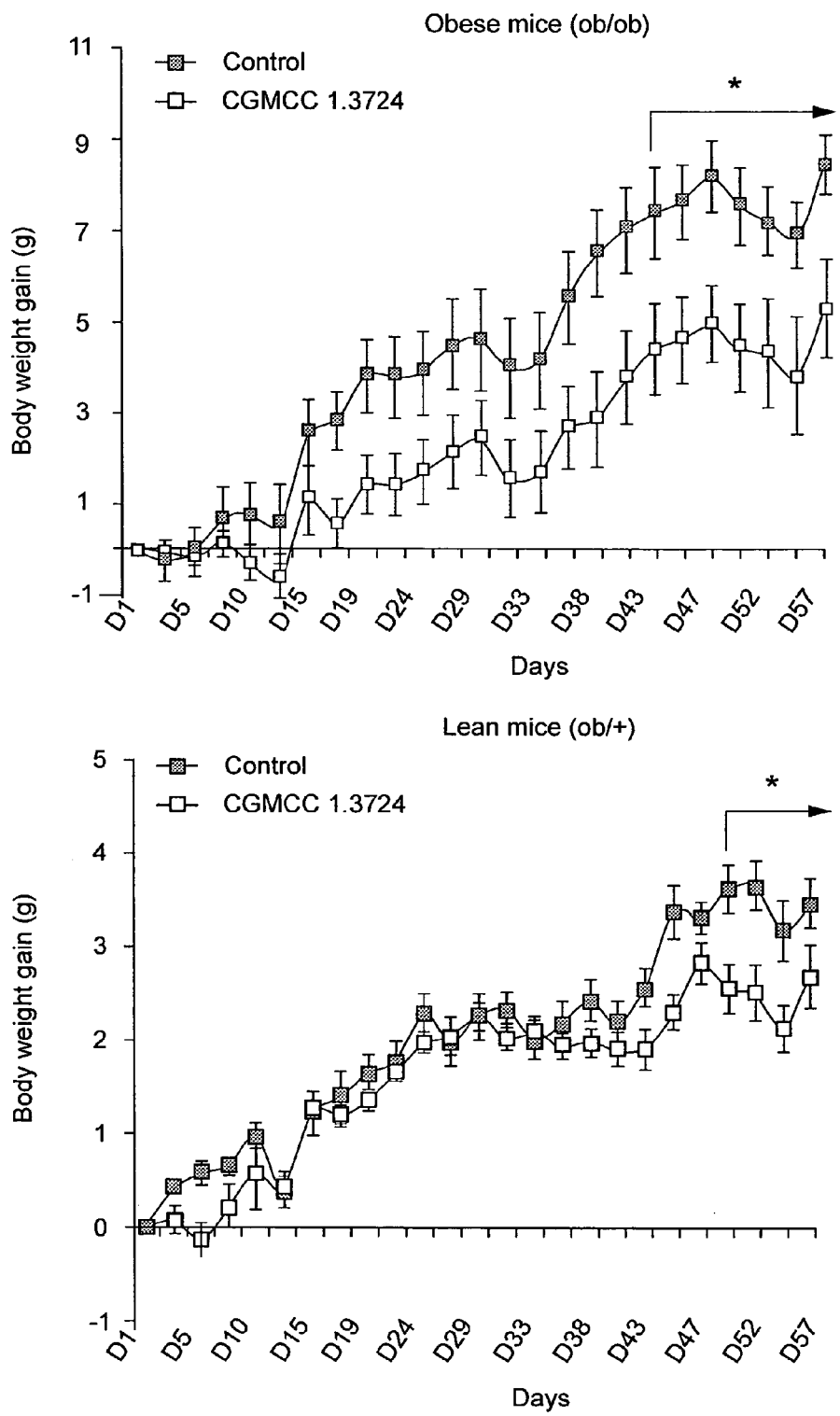
FIG. 4 shows the body weight gain of obese and lean mice with time.

Body weight gain of both obese (ob/ob) and lean (ob/+) mice receiving CGMCC 1.3724 in the drinking solution was reduced respectively by 37% and 22%, as compared with their respective control groups (FIG. 4).

Figure 5:
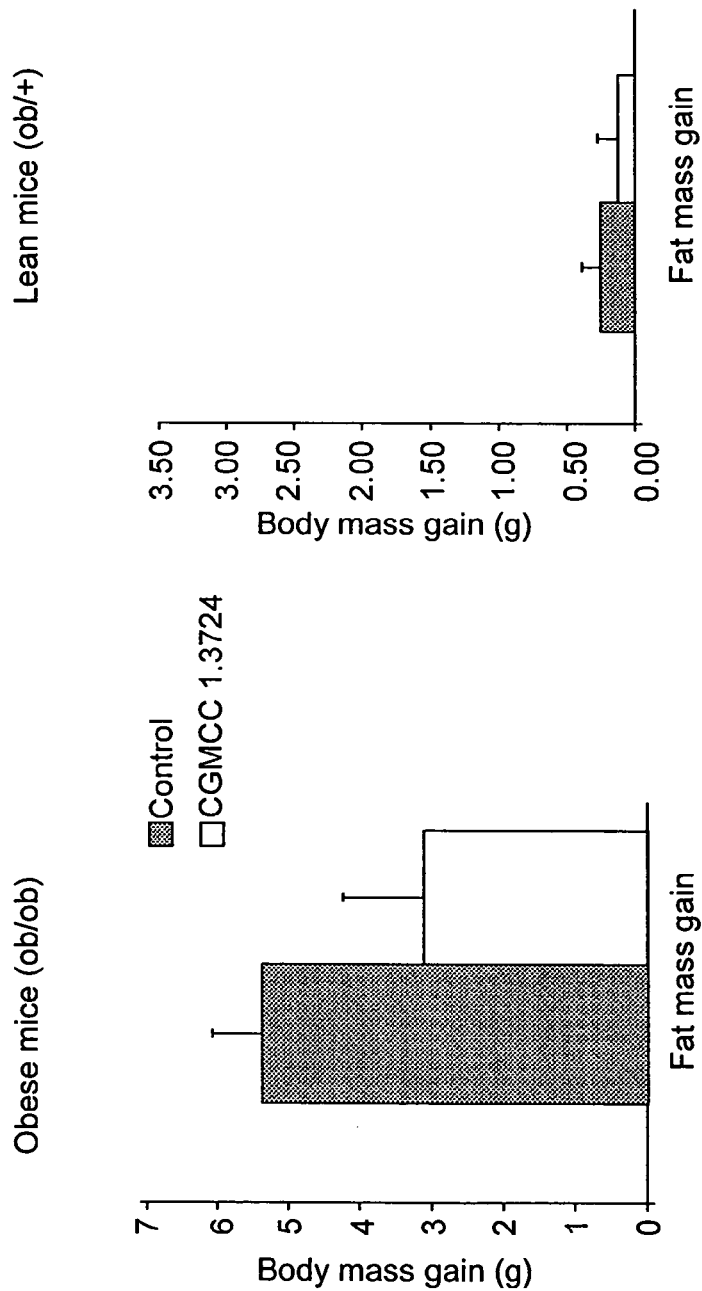
FIG. 5 shows the fat mass gain of obese and lean mice.

Administration of the CGMCC 1.3724 strain induced a reduction of fat mass gain in obese mice and to a lower extent in lean mice as compared to control animals (FIG. 5).

Identical Experiments with *Lactobacillus rhamnosus* NCC 4007 gave similar results.

The invention claimed is:

1. A method for weight loss and/or weight maintenance in a human or an animal comprising the step of administering to the human or animal a composition comprising *Lactobacillus rhamnosus* CGMCC 1.3724.

2. The method in accordance with claim 1, wherein the human is at least 2 years old.

3. The method in accordance with claim 1, wherein the composition is a medicament or a food product.

4. The method in accordance with claim 1, wherein the composition comprises at least one other food grade bacteria and/or yeast.

5. The method in accordance with claim 4, wherein the food grade bacteria is selected from the group consisting of lactic acid bacteria, bifidobacteria, propionibacteria and mixtures thereof.

6. The method in accordance with claim 1, wherein the composition further comprises at least one prebiotic.

7. The method in accordance with claim 6, wherein the prebiotic is selected from the group consisting of oligosaccharides and optionally contains fructose, galactose, mannose, soy, inulin; dietary fibers; and mixtures thereof.

8. The method in accordance with claim 1, wherein at least a part of the strain is alive in the composition.

9. The method in accordance with claim 1, wherein at least a part of the strain is not alive in the composition.

10. The method in accordance with claim 1, wherein the composition is a medicament and comprises between $10^2$ and $10^{12}$ cfu of *Lactobacillus rhamnosus* CGMCC 1.3724 per daily dose.

11. The method in accordance with claim 1, wherein the composition is a food product and comprises between $10^3$ and $10^{12}$ cfu of *Lactobacillus rhamnosus* CGMCC 1.3724 per g of the dry weight of the food composition.

12. The method in accordance with claim 1, wherein the human is an adult.

13. A method of treating obesity comprising the step of administering to an obese individual a composition comprising *Lactobacillus rhamnosus* CGMCC 1.3724.

14. A method for treating metabolic disorders comprising the steps of administering to an individual suffering from same a composition comprising *Lactobacillus rhamnosus* CGMCC 1.3724.

15. The method in accordance with claim 14, wherein the metabolic disorders is selected from the group consisting of diabetes, hypertension and cardiovascular diseases.

* * * * *